(12) United States Patent
McInnes et al.

(10) Patent No.: US 10,449,349 B2
(45) Date of Patent: Oct. 22, 2019

(54) SYSTEMS, DEVICES, AND METHODS INCLUDING ENCAPSULATED COSMETICS

(71) Applicant: L'Oreal, Paris (FR)

(72) Inventors: James Christopher McInnes, Seattle, WA (US); John Streeter, Redmond, WA (US); Vincenzo Casasanta, III, Woodinville, WA (US)

(73) Assignee: L'Oreal, Paris (FR)

( * ) Notice: Subject to any disclaimer, the term of this patent is extended or adjusted under 35 U.S.C. 154(b) by 338 days.

(21) Appl. No.: 15/379,346

(22) Filed: Dec. 14, 2016

(65) Prior Publication Data
US 2018/0161564 A1 Jun. 14, 2018

(51) Int. Cl.
| A61M 37/00 | (2006.01) |
| A61K 49/22 | (2006.01) |
| A61K 41/00 | (2006.01) |
| A61N 7/00 | (2006.01) |
| A61Q 1/02 | (2006.01) |
| A61K 8/02 | (2006.01) |
| A61K 8/14 | (2006.01) |

(52) U.S. Cl.
CPC ....... *A61M 37/0092* (2013.01); *A61K 8/0291* (2013.01); *A61K 8/14* (2013.01); *A61K 41/0033* (2013.01); *A61K 49/227* (2013.01); *A61M 37/0015* (2013.01); *A61M 37/0076* (2013.01); *A61N 7/00* (2013.01); *A61Q 1/02* (2013.01); *A61K 2800/43* (2013.01); *A61K 2800/82* (2013.01); *A61M 2037/0007* (2013.01); *A61M 2037/0023* (2013.01); *A61M 2037/0061* (2013.01); *A61M 2205/50* (2013.01); *A61M 2205/52* (2013.01); *A61N 2007/0039* (2013.01)

(58) Field of Classification Search
CPC .......... A61M 37/0092; A61M 37/0015; A61M 37/0076; A61M 2037/0007; A61M 2037/0061; A61M 2205/50; A61M 2205/52; A61M 2037/0023; A61N 7/00; A61N 2007/0039; A61Q 1/02; A61K 8/0291; A61K 8/14; A61K 49/227; A61K 41/0033; A61K 2800/43; A61K 2800/82

See application file for complete search history.

(56) References Cited

U.S. PATENT DOCUMENTS

| 6,649,702 B1 | 11/2003 | Rapoport et al. |
| 8,999,295 B2 | 4/2015 | Pitt et al. |
| 2004/0228817 A1 | 11/2004 | Simon et al. |
| 2004/0228818 A1 | 11/2004 | Simon et al. |
| 2008/0254077 A1 | 10/2008 | Prigent |
| 2009/0246270 A1 | 10/2009 | Jones |
| 2012/0156269 A1 | 6/2012 | Simonnet et al. |

(Continued)

OTHER PUBLICATIONS

Couture, O., et al., "Review of Ultrasound Mediated Drug Delivery for Cancer Treatment: Updates From Pre-Clinical Studies," Translational Cancer Research 3(5):494-511, Oct. 2014.

(Continued)

*Primary Examiner* — Rex R Holmes
(74) *Attorney, Agent, or Firm* — Christensen O'Connor Johnson Kindness PLLC

(57) ABSTRACT

Single layer and multilayer vesicles with actives inside are delivered into living tissue. Then, the vesicles are disrupted using ultrasound. The vesicles are used to create an image in the tissue or for the delivery of certain actives to the skin.

18 Claims, 4 Drawing Sheets

(56) References Cited

U.S. PATENT DOCUMENTS

2014/0046181 A1  2/2014  Benchimol et al.
2014/0066837 A1  3/2014  Moy
2014/0112921 A1* 4/2014  Ross ................. A61M 37/0015
                                                    424/134.1
2014/0147390 A1  5/2014  Exner et al.
2016/0184193 A1* 6/2016  Casasanta, III .......... A61K 8/60
                                                    601/2

OTHER PUBLICATIONS

International Search Report and Written Opinion dated Mar. 22, 2018, issued in corresponding International Application No. PCT/US2017/065630, filed Dec. 11, 2017, 20 pages.

Bhatnagar, S., et al., "Exploitation of Sub-Micron Cavitation Nuclei to Enhance Ultrasound-Mediated Transdermal Transport and Penetration of Vaccines," Journal of Controlled Release 238:22-30, Sep. 2016.

Kwan, J.J., et al., "Ultrasound-Propelled Nanocups for Drug Delivery," Small 11(39):5305-5314, Oct. 2015.

Zhang, K., et al., "$CO_2$ Bubbling-Based 'Nanobomb' System for Targetedly Suppressing Panc-1 Pancreatic Tumor Via Low Intensity Ultrasound-Activated Inertial Cavitation," Theranostics 5(11):1291-1302, Sep. 2015.

* cited by examiner

SYSTEMS, DEVICES, AND METHODS INCLUDING ENCAPSULATED COSMETICS

SUMMARY

In an aspect, the present disclosure is directed to, among other things, a method of creating an image on living tissue includes applying a composition to living tissue, the composition including a plurality of sonosensitive vesicles containing actives; and applying ultrasound selectively to the living tissue via a 2D ultrasound array to release the actives from the vesicles sensitive to the ultrasound energy and create an image on the living tissue.

In an embodiment, the method includes applying a composition having a plurality of sonosensitive vesicles containing colorants.

In an embodiment, the method includes applying a composition having a plurality of sonosensitive micelles or sonosensitive liposomes.

In an embodiment, the method includes applying a composition having a first plurality of vesicles containing a first active and a second plurality of vesicles containing a second active.

In an embodiment, the first plurality of vesicles is sensitive to ultrasound of a first frequency range, and the second plurality of vesicles is sensitive to ultrasound of a second frequency range.

In an embodiment, the vesicles include an exterior layer and an interior layer, and a first active is contained on the inside of the interior layer, and a second active is contained between the exterior and interior layer, and the method further comprises applying ultrasound at a frequency range to release the first active from the interior layer to mix with the second active within the exterior layer.

In an embodiment, the first active is a first color and the second active is a second color, wherein mixing of the first and second actives produces a third color.

In an embodiment, the vesicles include an exterior layer and an interior layer, and a first active is contained on the inside of the interior layer, and a second active is contained between the exterior and interior layers, and the method further comprises applying ultrasound at a first frequency range to release the second active from between the interior and exterior layers to form the image in the living tissue.

In an embodiment, the method further comprises applying ultrasound at a second frequency range to release the first active which neutralizes the second active in the living tissue.

In an embodiment, ultrasound is defined as a frequency greater than 20 kilohertz.

In an aspect, the present disclosure is directed to, among other things, a method of dispensing an active to living tissue including dispensing into living tissue a plurality of sonosensitive vesicles containing an active, wherein the vesicles are dispensed into the living tissue via plurality of microneedles varying in diameter or length or both diameter and length; and applying ultrasound selectively to the living tissue via a 2D ultrasound transducer array.

In an embodiment, the method further comprises depositing vesicles at more than one depth in the living tissue.

In an embodiment, the method further comprises adjusting a focal length of the 2D ultrasound transducer array to target vesicles at a first depth.

In an embodiment, the method further comprises depositing vesicles over an area at the same depth, wherein higher concentrations of vesicles are created in the area.

In an embodiment, the method further comprises selectively turning on 2D transducer array elements to target the areas having a greater concentration of vesicles.

In an embodiment, the method further comprises adjusting a frequency of the 2D transducer array to sensitize less than all the vesicles to cause a release of actives.

In an embodiment, the vesicles include micelles, reverse micelles, liposomes, niosomes, hydrogels, hydrophobic polymers, or any combination thereof.

In an aspect, the present disclosure is directed to, among other things, a method of dispensing a peptide or protein to living tissue including dispensing into living tissue a plurality of sonosensitive vesicles containing a peptide or protein or both; and applying ultrasound selectively to the living tissue via a 2D ultrasound transducer array to cause release of the peptide, protein, or both. In an embodiment, the vesicle is a reverse micelle, a liposome, or a hydrogel.

In an aspect, the present disclosure is directed to, among other things, a composition including a sonosensitive vesicle having one or more layers formed by amphipathic molecules, a sonosensitizer agent, and a colorant is within at least one layer. In an embodiment, the composition is a micelle. In an embodiment, the composition is a liposome. In an embodiment, the liposome has a first interior layer, a second exterior layer concentric with the first layer, a first colorant within the first layer, and a second colorant between the first and second layers. In an embodiment, the first and second colorant produce a third colorant when mixed. In an embodiment, the second colorant is a neutralizing pigment that hides the color of the first colorant.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Two-dimensional (2D) ultrasound devices have transducer elements arranged in arrays which extend in two mutually transverse directions. The transducer elements generate sound waves in the ultrasonic range, for example. In an embodiment, the 2D array is constructed with any number of transducer elements in each direction. The 2D transducer arrays are controlled by switching on and off the individual transducer elements according to a pre-determined schedule or program of pulses. In addition, in an embodiment, each individual transducer element is individually controlled for frequency, amplitude, power density, pulse period, temperature, direction, and focus. A 2D ultrasound device for use in the embodiments of this disclosure will be understood from the description herein. In an embodiment, each individual transducer element in a 2D ultrasound transducer array is individually controlled for frequency. In an embodiment, each individual transducer element in a 2D ultrasound transducer array is individually controlled for amplitude. In an embodiment, each individual transducer element in a 2D ultrasound transducer array is individually controlled according to one or more pulse parameters. In an embodiment, each individual transducer element in a 2D ultrasound transducer array is individually controlled for power density. In an embodiment, each individual transducer element in a 2D ultrasound transducer array is individually controlled for pulse period. In an embodiment, each individual transducer element in a 2D ultrasound transducer array is individually controlled for temperature. In an embodiment, each individual transducer element in a 2D ultrasound transducer array is individually direction controlled. In an embodiment, each individual transducer element in a 2D ultrasound transducer array is individually controlled for focus to give a wide or narrow focal point. In an embodiment, each individual transducer element in a 2D ultrasound transducer array is individually controlled for focus to change the depth of the focal point.

Figure 1:
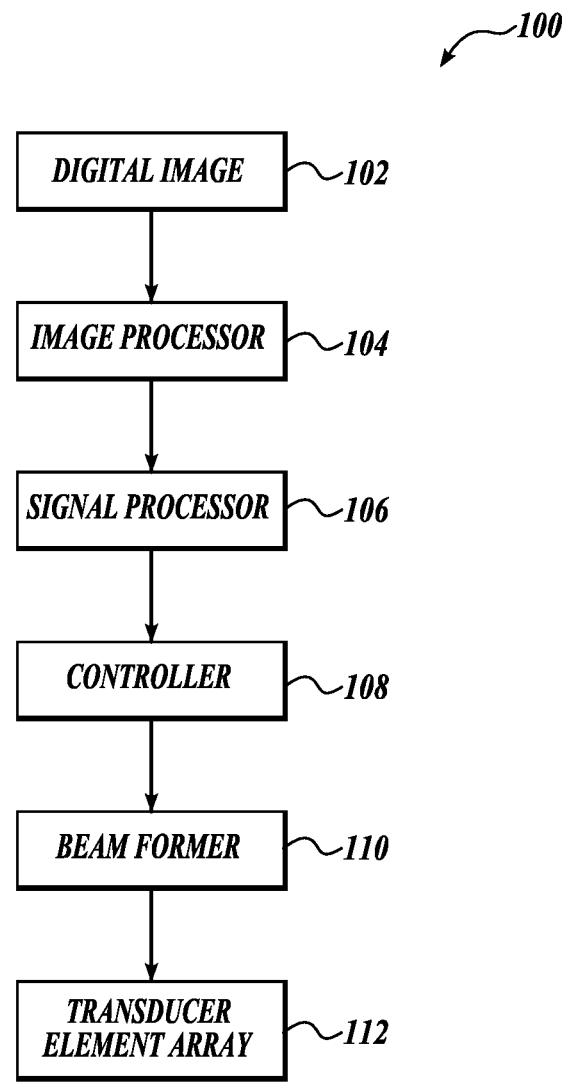
FIG. 1 is a flow diagram of an embodiment of a method to deliver an active to living tissue via sonosensitive vesicles.

Referring to FIG. 1, in an embodiment, a 2D ultrasound transducer system 100 for use with the embodiments disclosed herein includes a memory or storage 102 for storing a digital image, an image processor 104 to convert the digital image into signals, such as a raster image or bitmap, a signal processor 106 for processing the raster image or bitmap into signals that is interpreted by a controller 108, a beamformer 110 that is instructed by the controller to switch on and off the individual transducer elements, and a 2D array of transducer elements 112. In an embodiment, the controller 108 instructs the beamformer 110 to change the time, frequency, amplitude, direction, and focus of the individual transducer elements. It is to be appreciated that other suitable 2D ultrasound transducer systems include fewer or more features, as the illustrated system 100 is being shown as a representative embodiment.

In an embodiment, the 2D ultrasound transducer receives a digital image, and through an image processor and signal processor transforms the digital image into a set of commands that are interpreted by the beamformer to send the appropriate control signals that directs the individual transducer elements to turn on, how long to stay on, and to control the frequency, amplitude, direction, and focus. In an embodiment, the initial digital image 102 supplied to the 2D transducer array system is created on a computer or digital camera, or is a scan of a conventional photograph. As will be discussed further below, the 2D ultrasound transducer system will be used in a method that allows the reproduction of images on living tissue, such as skin, for the purposes of recreating the image, for applying long-lasting or permanent color cosmetics, or for the delivery of beneficial substances to the dermis or epidermis, among other beneficial uses. In an embodiment, the ultrasound transducer has a linear row of transducers. In an embodiment, the ultrasound transducer uses only a single transducer element. Further, in an embodiment, the ultrasound transducer is used to push, direct, or cause the migration of vesicles into living tissue. In an embodiment, ultrasound is used for sonophoresis. In an embodiment, low frequency acoustic energy is also used for sonophoresis.

As disclosed herein, vesicles include a payload of actives. In an embodiment, the vesicles are first delivered into living tissue, such as the skin. Then, once in the skin, the application of acoustic energy directed to the vesicles will cause the release of the payload, i.e., release the actives from the vesicles.

Figure 2:
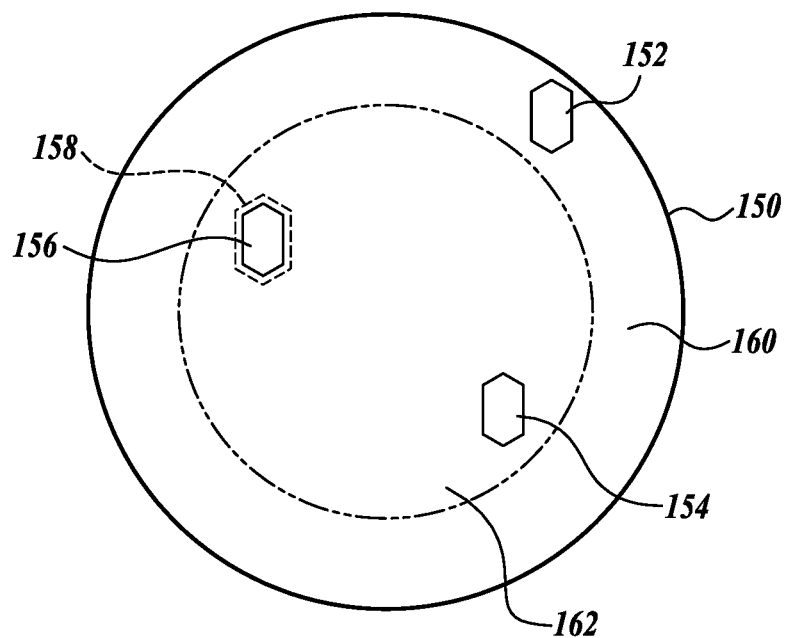
FIG. 2 is a diagrammatical illustration of an embodiment of a vesicle having more than one sonosensitizer.

FIG. 2 is a diagrammatical illustration of a generalized vesicle 160. In an embodiment, a vesicle 160 is a solid particle having one or more actives in or on the particle. In an embodiment, a vesicle is sensitive to ultrasound of certain parameters, wherein the ultrasound will cause release of the actives. In an embodiment, a vesicle contains a sonosensitizer that is sensitive to ultrasound that causes release of the actives. In an embodiment, the vesicle itself is made sensitive to ultrasound to release the active.

Figure 3:
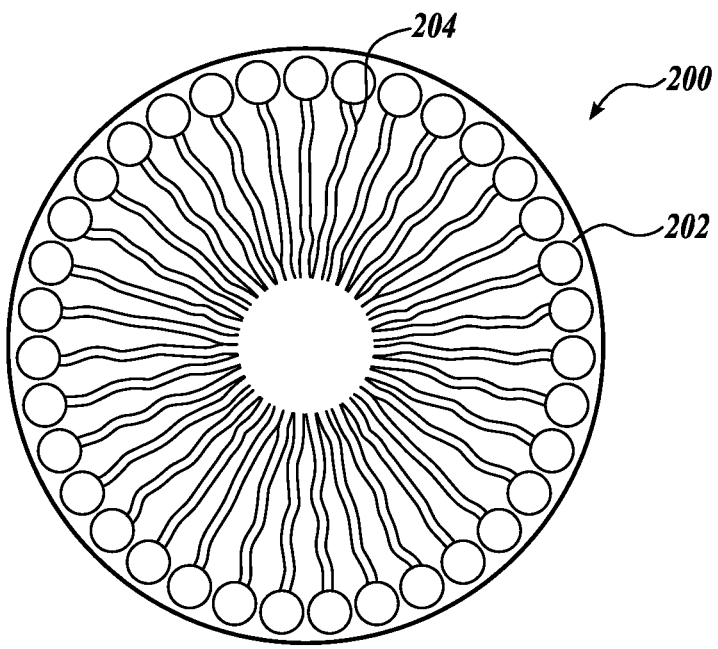
FIG. 3 is a diagrammatical illustration of an embodiment of a sonosensitive micelle.
Figure 4:
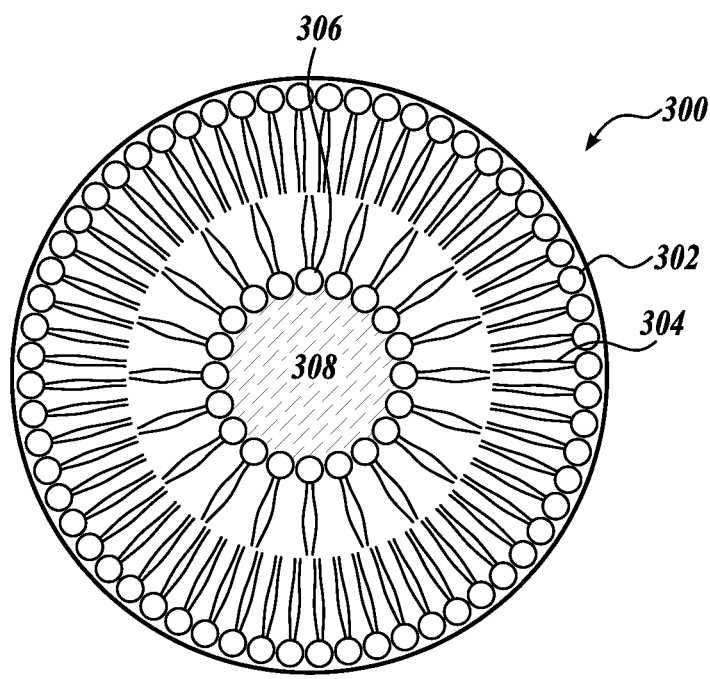
FIG. 4 is a diagrammatical illustration of an embodiment of a sonosensitive liposome.

In an embodiment, a vesicle is a micelle or liposome. Micelles and liposomes have amphipathic molecules creating a layered structure. An amphipathic molecule has a hydrophilic part connected to a hydrophobic part. A micelle has a single layer of such molecules, while a liposome has two concentric layers of molecules. Multilayered vesicles of three more layers are also possible. Referring to FIG. 3, in an embodiment of a micelle 200, the hydrophilic parts 202 of molecules are exposed on the exterior, while the hydrophobic parts 204 of the molecules are in the center of the micelle. Referring to FIG. 4, in an embodiment of a liposome 300, two concentric layers (lamellae) of amphipathic molecules are arranged, wherein the hydrophilic parts 302 of the molecules of the first outer layer are exposed on the exterior surface. The hydrophilic parts 306 of the molecules of the second inner layer form an inner core area 308. The hydrophobic parts 304 of the molecules of both layers are between the two hydrophilic parts 302 and 306 of the outer layer and inner core. "Reverse" or "inverted" micelles have the hydrophobic part of the molecule on the exterior and the hydrophilic part is in the interior. In an embodiment, micelles 200 and liposomes 300 are made with at least one active on the inside. In addition, micelles 200 and liposomes 300 are made to be sensitive to ultrasound. Niosomes are also lamellar structures. Niosomes are a non-ionic vesicle. In an embodiment, a noisome is formed by a non-ionic surfactant and an expedient, such as cholesterol. Like liposomes, niosomes have a bilayer of molecules, wherein in the exterior layer, the hydrophilic parts of the molecules are on the exterior, and the hydrophobic parts point inward. In the second inner layer, the hydrophilic parts of the molecules point inward, and the hydrophobic parts of the molecules point toward the hydrophobic parts of the molecules of the first exterior layer. Thus, making an aqueous region in the center.

In an embodiment, a vesicle is made from a hydrophobic polymer. In an embodiment, a vesicle is made from poly (lactic-co-glycolic acid), also known as PLGA. In an embodiment, a vesicle is made from a hydrogel.

As described, a vesicle can be one of many forms. In an embodiment, a vesicle is a liposome. In an embodiment, a vesicle is a liposome with a perfluorocarbon nanoemulsion. In an embodiment, a vesicle is a micelle. In an embodiment, a vesicle is a micelle with a low critical solution temperature hydrogel. In an embodiment, a vesicle is a niosome. In an embodiment, a vesicle is a hydrophobic polymer. In an embodiment, a vesicle has a lamellar structure. The number of lamellae are not limited. In an embodiment, when there are two or more lamellae, the lamellae are concentric. In an embodiment, a vesicle does not have a lamellar structure. In an embodiment, a vesicle has an aqueous region on the inside of the vesicle. In an embodiment, a vesicle comprises pores.

In the embodiments described herein that use a vesicle, the vesicle can be selected from any one or a combination of vesicles described herein. However, a vesicle includes any other encapsulating structure that is capable of serving the function of a vesicle as described herein. The types of vesicles described herein are made sensitive to ultrasound to cause release of the active inside the vesicle. That is, when exposed to acoustic energy of a certain parameter or parameters, the vesicle will release one or more actives. In an embodiment, a vesicle includes a sonosensitizer. In the case where a vesicle includes a sonosensitizer, the sonosensitizer is sensitive to acoustic energy, such as ultrasound. In an embodiment, the vesicle itself is sensitive to acoustic energy, such as ultrasound. In an embodiment where the vesicle itself is sensitive to acoustic energy, the vesicle may not have a sonosensitizer.

Referring to FIG. 2, a diagrammatical illustration of a generalized vesicle 150 is illustrated. The vesicle 150 is representative of vesicle types. In an embodiment, the vesicle 150 has a lamellar structure represented by the layer 160. In an embodiment, the vesicle 150 has an aqueous region 162 on the inside of the vesicle. FIG. 2 is meant to represent various types of sonosensitizers in or on the vesicle 150 that render the vesicle sensitive to acoustic energy, such as ultrasound. In an embodiment, a sonosensitizer 152 is included in a layer 160 of the vesicle 150. In an embodiment, a sonosensitizer 154 is included in a core region 162 of the vesicle 150. In an embodiment, where the vesicle is non-layered, a sonosensitizer can be uniformly or non-uniformly distributed throughout the vesicle 150. In an embodiment, the active 158 is bonded to the sonosensitizer 156.

Non-limiting examples of sonosensitizers include covalently bonded assemblies of molecules (e.g., hydrophobic and hydrophilic polymers), non-covalently bonded (e.g., ionically bonded, hydrogen bonded) assemblies of molecules (e.g., polymers), complexes, macromolecules, and the like. In an embodiment, a sonosensitizer is a solid particle. In an embodiment, a sonosensitizer undergoes a phase change from solid to liquid when irradiated with acoustic energy. In an embodiment, a sonosensitizer undergoes a phase change from liquid to gas when irradiated with acoustic energy.

In an embodiment, a sonosensitizer is a hydrogel. In an embodiment, a sonosensitizer is a low critical solution temperature hydrogel. In an embodiment, the low critical solution temperature hydrogel collapses upon heating with acoustic energy. A method for the manufacture of vesicles, including micelles, with low critical solution temperature hydrogels is disclosed in U.S. Pat. No. 6,649,702, incorporated herein expressly by reference for all purposes.

In an embodiment, a sonosensitizer is a liquid. In an embodiment, a sonosensitizer is a nanoemulsion of a perfluorocarbon liquid. In an embodiment, the perfluorocarbon undergoes a phase change from liquid to gas upon the application of acoustic energy, including ultrasound. In an embodiment, the perfluorocarbon is selected from perfluoroheptane, perfluorohexane, perfluoropentane, perfluorobutane, perfluoroether or a combination thereof. A method for the manufacture of vesicles, including liposomes, with perfluorocarbon nanoemulsions is disclosed in U.S. Pat. No. 8,999,295, incorporated herein expressly by reference for all purposes.

Figure 5:
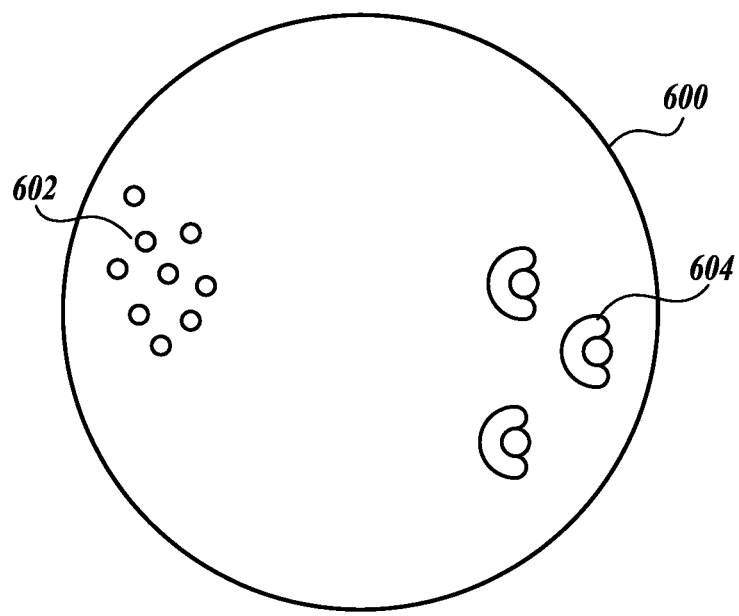
FIG. 5 is a diagrammatical illustration of an embodiment of a vesicle having more than one cavitation enhancer.

In an embodiment, sonosensitizers are cavitation enhancers. In an embodiment, vesicles are disrupted and will collapse by shear forces caused by cavitation. In an embodiment, acoustic energy, including ultrasound, causes cavitation and collapse of vesicles, thus, releasing the active. Referring to FIG. 5, a vesicle 600 including sonosensitizers used as cavitation enhancers include microbubbles 602 and solid-gas nano particles or mesoporous nanoparticles 604. In an embodiment, hollow mesoporous silica nanoparticles carrier and L-arginine are capable of producing carbon dioxide bubbles in response to pH and/or temperature. In an embodiment, solid-gas nanoparticle cavitation enhancers 604 are made from polystyrene coated with methylmethacrylate with a divinylbenzene crosslinker. The solid "cup" traps a gas bubble within a cavity. Upon the application of ultrasound, the bubble grows and detaches from the cup, and eventually collapses due to the compression phase of ultrasound. In an embodiment, this cavitation is used to cause the release of actives from vesicles.

In an embodiment, when microbubbles are irradiated with acoustic energy, such as ultrasound, the bubbles will undergo vibration. The vibration results in membrane permeabilization in the regions surrounding the bubbles and the release of the actives from the vesicles. In an embodiment, vesicle membranes are ruptured or pores are created in the vesicles leading to the release of the actives.

In an embodiment, vesicles do not include sonosensitizers, because the vesicles themselves are sensitive to acoustic energy. In an embodiment, the vesicles are made sensitive to a certain frequency range by controlling the molecular weight of the amphipathic molecules that make up the vesicles. In an embodiment, the vesicles are caused to release the actives inside by the application of ultrasonic cavitation.

Acoustic energy for releasing the actives of vesicles includes, but is not limited to acoustic energy in the ultrasound range. Different sonosensitizers will be sensitive to different ultrasound parameters. Similarly, different vesicles will be sensitive to different ultrasound parameters. In an embodiment, ultrasound parameters include, but are not limited to, frequency, amplitude, power density, duty cycle, pulse period, and temperature. The different sonosensitizers or vesicles are tuned to be sensitive to one or a combination of frequency, amplitude, power density, duty cycle, pulse period, and temperature.

In an embodiment, vesicles made in accordance with this disclosure are made sensitive to ultrasound frequencies in order to cause a release of an active from the vesicle. In an embodiment, ultrasound has a frequency greater than an audio frequency of 20 kilohertz. In an embodiment, ultrasound has a frequency greater than 2 megahertz. In an embodiment, ultrasound has a frequency greater than 200 megahertz. In an embodiment, ultrasound includes any range from 20 kilohertz or greater. In an embodiment, ultrasound includes any range derivable inbetween 20 kilohertz to 200 megahertz. In an embodiment, ultrasound is high intensity focused ultrasound (HIFU), high intensity non-focused ultrasound, or a combination of both.

In an embodiment, the ultrasound power density is up to 100 Watt/cm$^2$. In an embodiment, the ultrasound power density is up to 90 Watt/cm$^2$. In an embodiment, the ultrasound power density is up to 80 Watt/cm$^2$. In an embodiment, the ultrasound power density is up to 70 Watt/cm$^2$. In an embodiment, the ultrasound power density is up to 60 Watt/cm$^2$. In an embodiment, the ultrasound power density is up to 50 Watt/cm$^2$. In an embodiment, the ultrasound power density is up to 40 Watt/cm$^2$. In an embodiment, the ultrasound power density is up to 30 Watt/cm$^2$. In an embodiment, the ultrasound power density is up to 20 Watt/cm$^2$. In an embodiment, the ultrasound power density is up to 10 Watt/cm$^2$.

In an embodiment, the duty cycle is 100%. When the duty cycle is 100%, the waveform is continuous. In an embodiment, the waveform includes pulses. In an embodiment, the duty cycle is 90%. In an embodiment, the duty cycle is 80%. In an embodiment, the duty cycle is 70%. In an embodiment, the duty cycle is 60%. In an embodiment, the duty cycle is 50%. In an embodiment, the duty cycle is 40%. In an embodiment, the duty cycle is 30%. In an embodiment, the duty cycle is 20%. In an embodiment, the duty cycle is 10%.

In an embodiment, the sonosensitizer is sensitive to ultrasound pulses. Ultrasound waves have a low pressure region. In an embodiment, some sonosensitizers are sensitive to pulses of low pressure. In an embodiment, the pulse period is from 0.01 seconds to 1,000 seconds. In an embodiment, the pulse period is less than 100 seconds. In an embodiment, the pulse period is less than 90 seconds. In an embodiment, the pulse period is less than 80 seconds. In an embodiment, the pulse period is less than 70 seconds. In an embodiment, the pulse period is less than 60 seconds. In an embodiment, the pulse period is less than 50 seconds. In an embodiment, the pulse period is less than 40 seconds. In an embodiment, the pulse period is less than 30 seconds. In an embodiment, the pulse period is less than 20 seconds. In an embodiment, the pulse period is less than 10 seconds. In an embodiment, the pulse period is less than 5 seconds. In an embodiment, the pulse period is less than 4 seconds. In an embodiment, the pulse period is less than 3 seconds. In an embodiment, the pulse period is less than 2 seconds. In an embodiment, the pulse period is less than 1 second. In an embodiment, a pulse is defined as a pulse group, which includes multiple cycles, a cycle being, for example, the length from peak-to-peak, trough-to-trough, or any two points in between. In an embodiment, the ultrasound waveform is a combination waveform including continuous wave, pulses, and pulse groups.

In an embodiment, sonosensitizers are sensitive to a particular frequency. In an embodiment, sonosensitizers are sensitive to a particular amplitude. In an embodiment, sonosensitizers are sensitive to a particular pulse. In an embodiment, sonosensitizers are sensitive to a particular temperature. In an embodiment, sonosensitizers are sensitive to a particular power density. In an embodiment, sonosensitizers are sensitive to more than one of the ultrasound parameters. In an embodiment, the sonosensitizer is inside, on the surface, or within the layers of the vesicles. In an embodiment, when a sonosensitizer is exposed to ultrasound of a certain ultrasound parameter or parameters to sensitize the sonosensitizer, the sonosensitizer increases the permeability of the layers to enable the active that is within the layers to be released from the layer. In an embodiment, the active resides in the hydrophobic parts of amphipathic molecules. In an embodiment, the active resides in the hydrophilic parts of amphipathic molecules. In an embodiment, actives reside within the center core of vesicles. In an embodiment, the same or different actives reside simultaneously within the hydrophobic parts and the center core of vesicles. In an embodiment, the first active and the second active do not react with each other. In an embodiment, the first active and the second active are brought into contact to mix or react with each other when the vesicles are treated with ultrasound.

In an embodiment, actives include dyes, cosmetics, colorants, peptides, proteins, ceramides, medicaments, therapeutic agents, beneficial substances, and other actives that are applied to living tissue, for example, to the skin. In an embodiment, the actives are delivered to the skin including the dermis or epidermis or both via the use of sonosensitive vesicles including sonosensitive micelles and sonosensitive liposomes coupled with the use of an ultrasound transducer. In an embodiment, ultrasound transducers include 2D, linear, or a single transducer arrangement. In this disclosure, "vesicles" includes micelles, liposomes, hydrogels, and niosomes, unless, clearly indicated to be a particular vesicle based on the particular context. In this disclosure, "vesicles" also includes other encapsulating structures that are not micelles, liposomes, hydrogels, or niosomes, but that encapsulate an active and are sensitive to ultrasound. In an embodiment, an aqueous active is in the core 308 of the liposome 300. In an embodiment, a lipid soluble active is in the hydrophobic bilayer 304 of the liposome 300. In an embodiment, a lipid soluble active is in the hydrophobic layer 204 of the micelle 200. In an embodiment, an aqueous active is in the interior layer of a reverse micelle. In an embodiment, the type and characteristics of the active desired to be delivered to the living tissue will dictate the amphipathic molecule for creating the micelle or liposome encapsulating such active.

In an embodiment, suitable amphipathic molecules for forming micelles and liposomes in accordance with this disclosure include a hydrophilic part and a hydrophobic part. In an embodiment, the hydrophobic part is a straight or branched hydrocarbon. In an embodiment, the hydrophobic part is described by the formula $CH_3(CH_2)_n$, wherein n is greater than 2. In an embodiment, the hydrophilic part includes charged groups, including anionic and cationic groups. In an embodiment, the hydrophilic part includes a group selected from an ammonium group ($RNH_3^+$), a carboxylate group ($RCO_2^-$), a sulfate group ($RSO_4^-$), a sulfonate group ($RSO_3^-$), and a phosphate group ($PO_4^{3-}$). In an embodiment, the hydrophilic group includes uncharged polar groups, including alcohols.

In an embodiment, a sonosensitive micelle or liposome with an active inside is made generally by a method that involves the following steps. In an embodiment, the amphipathic molecules are mixed with an organic solvent. Organic solvents include, but are not limited to, chloroform, methanol, tertiary butanol, cyclohexane, or mixtures thereof. The solvent is then removed leaving a film. The film is then dried and lyophilized. Thereafter, hydration of the film is done by addition of the aqueous medium combined with agitation at a temperature above the gel-liquid crystal transition temperature. In an embodiment, the aqueous medium includes the desired active. Hydration time and temperature will vary for the different amphipathic molecules. The process results in large multilamellar vesicles. Disruption of the large multilamellar vesicles by sonication or extrusion is used to produce the smaller micelles and liposomes.

In an embodiment, in order to tune the vesicles to be sensitive at certain frequency ranges, the size of the vesicles is controlled. In an embodiment, the size of the vesicle determines the resonant frequency. In an embodiment, the size of the vesicle is controlled within the resonant frequency range by extruding the large multilamellar vesicles through a filter having a defined pore size. The vesicles are disrupted by applying an ultrasound frequency at which the vesicle will continue to oscillate. At the resonant frequency, the vesicle will break down causing a release of the active inside.

In an embodiment, some vesicles undergo a phase change by the application of ultrasound causing a release of the actives inside. In an embodiment where the vesicle includes two or more concentric layers, the phase change of one layer occurs at a different ultrasound parameter compared to the second layer. In an embodiment, an inner layer is disrupted first allowing the mixing of a first and a second active within the vesicle. Then, the second outer layer is disrupted causing the release of the mixed actives from the vesicle. In an embodiment, an outer layer is disrupted first allowing the release of the first active. Then, the second inner layer is disrupted causing the release of the second active that then reacts with or otherwise affects the first active.

In an embodiment, the frequency of the ultrasound will determine the depth at which an active is released. In an embodiment, lower frequencies of ultrasound penetrate deeper in the tissue; therefore, lower frequencies are used for releasing actives from deeper in the tissue. In an embodiment, higher frequencies of ultrasound do not penetrate as deep as lower frequencies; therefore, higher frequencies are used for releasing actives from shallower depths in the tissue.

In an embodiment, the sonosensitive vesicles with actives are applied to living tissue via a microneedle array. In an embodiment, a microneedle array includes a plurality of needles of the same diameter and length, such that the composition with sonosensitive vesicles is applied in a uniform concentration over area and depth. In an embodiment, a microneedle array includes a plurality of needles of different diameters, such that the composition with sonosensitive vesicles is applied non-uniformly over an area, where the placement of the large diameter needles dictates a greater concentration of sonosensitive vesicles. In an embodiment, a microneedle array includes a plurality of needles of different lengths, such that the composition with sonosensitive vesicles is applied non-uniformly in the depth direction over an area, where the placement of the longer needles dictates sonosensitive vesicles placed deeper into the living tissue. In an embodiment, a microneedle array includes a plurality of needles of different diameters and different lengths, such that the composition with sonosensitive vesicles is applied non-uniformly over an area and volume, where the placement of the large diameter needles dictates a greater concentration of sonosensitive vesicles, and the longer needles dictate placement of vesicles deeper into the living tissue. In this way, reservoirs of vesicles varying in the amount of therapeutic agent over an area or depth in the living tissue are formed and the delivery of the actives within the vesicles is varied over an area and depth. In an embodiment, microneedles include hollow needles through which a composition of vesicles is introduced to the skin. In an embodiment, microneedles are solid needles that have the vesicles on the surface. In an embodiment, microneedles have a tip or section coated or otherwise adhering the vesicles, such that when the tip or section breaks off in the skin, the vesicles are delivered.

By using needles of different diameter, the amount of vesicles and thus, the actives delivered into the living tissue are greater for larger diameter needles and smaller for the smaller needles. This allows placing a greater amount of actives in specific areas where more actives are needed. When using different length microneedles, the different lengths allow placing the vesicles, and thus, the actives at various depths in the living tissue, such as in the dermis or epidermis.

While a microneedle array is disclosed as one possible alternative to applying sonosensitive vesicles to living tissue, the disclosure is not thereby limited, and other alternatives include single needles, or the application of gels, lotions, liquids, and the like that are formulated to penetrate into the skin to carry the sonosensitive vesicles.

In an embodiment, the vesicles are applied into living tissue via the use of iontophoresis. In iontophoresis, ionic vesicles are driven into living tissue by an applied electric field.

In an embodiment, the vesicles are applied into living tissue via the use of sonophoresis. Sonophoresis is a method of using ultrasound to stimulate vibrations in skin, for example, such that the kinetic energy of molecules is increased and also increases poration via cavitation.

In an embodiment, the vesicles are applied into living tissue via the combination of iontophoresis and sonophoresis.

Figure 6:
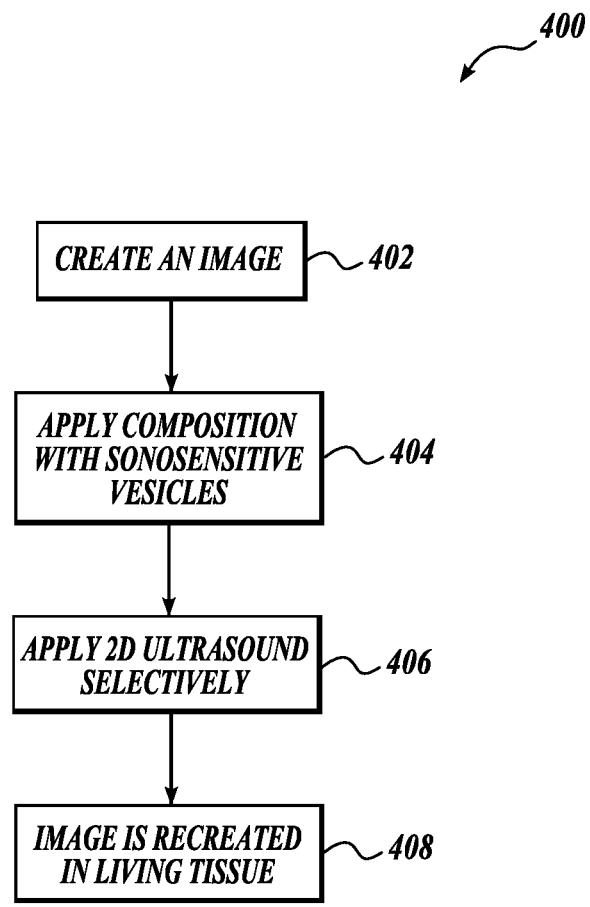
FIG. 6 is a diagrammatical illustration of an embodiment of a 2D ultrasound system.

Sonosensitive vesicles that can release actives have many uses. In an embodiment, the sonosensitive vesicles are used in a method of reproducing images in or on living tissue, such as skin. Reference to FIG. 6 will be used to describe such method.

In an embodiment, in step 402, a digital image is created. The digital image is stored as an electronic file. In an embodiment, the digital image is created using any photo editing software or computer-aided drawing software. In addition, digital images are created by digital cameras. As another alternative, a digital image is created by scanning any non-digital photographic print. There is no limitation on the manner in which digital images are created.

In an embodiment, the method includes a step 404 of applying a composition. In an embodiment, the composition includes a composition containing any of the sonosensitive vesicles with actives disclosed herein. In an embodiment, the composition includes water, oil, alcohol, or other agent as a vehicle for suspending the sonosensitive vesicles in the composition. In an embodiment, the composition is applied in or on living tissue in various forms. In an embodiment, a microneedle array is used to apply the composition percutaneously. In an embodiment, iontophoresis or sonophoresis or both are applied. In an embodiment, the composition is applied to the epidermis. In an embodiment, the composition is applied to the dermis. In an embodiment, the composition is applied topically. In an embodiment, the sonosensitive vesicles are distributed uniformly, such that there is minimal to no concentration gradient in the area of application. In an embodiment, the concentration per unit of area does not vary over the area of application. In an embodiment, the concentration per unit of volume does not vary over the volume of application. However, in an embodiment, the concentration of sonosensitive vesicles in the area of application varies. In an embodiment, the concentration of sonosensitive vesicles in the area of application varies over the area, such as the length or width or both. In an embodiment, the concentration of sonosensitive vesicles varies over the volume, such as in length, width, depth or all three within the living tissue.

In an embodiment, in step 406, energy in the ultrasound frequency range is applied selectively to the area or volume. In an embodiment, ultrasound energy is applied to cause the release of actives from the sonosensitive vesicles in a pattern selected to reproduce the digital image. In an embodiment, selectively applying ultrasound includes, for example, applying a different range of an ultrasound parameter from one or more of transducer elements in a 2D ultrasound array. In an embodiment, selectively applying ultrasound includes, for example, applying the same range of frequency from less than all transducer elements in a 2D ultrasound array. In an embodiment, selectively applying ultrasound includes, for example, applying a different amplitude from one or more of transducer elements in a 2D ultrasound array. In an embodiment, selectively applying ultrasound includes, for example, applying the same amplitude from less than all the transducer elements in a 2D ultrasound array. In an embodiment, selectively applying ultrasound includes, for example, applying a different frequency or amplitude or both from one or more of transducer elements in a 2D ultrasound array. In an embodiment, selectively applying ultrasound includes, for example, applying a different pulse from one or more of transducer elements in a 2D ultrasound array. In an embodiment, selectively applying ultrasound includes, for example, applying a different power density from one or more of transducer elements in a 2D ultrasound array. In an embodiment, selectively applying ultrasound includes, for example, heating to a different temperature from one or more of transducer elements in a 2D ultrasound array. In an embodiment, selectively applying ultrasound includes, for example, adjusting the focal length of one or more of transducer elements in a 2D ultrasound array. In an embodiment, the transducer does not have to be a 2D transducer array. In an embodiment, a single transducer element is used that is translated on the X-Y axes to apply ultrasound over an area.

In an embodiment, the image created in step 402 is recreated in step 408 by the application of the selective 2D ultrasound in step 406. In an embodiment, different sonosensitizers are sensitive to different frequency ranges. In an embodiment, a first sonosensitizer is used to form a vesicle containing a first colorant. In an embodiment, a second sonosensitizer is used to form a vesicle containing a second colorant. In an embodiment, a third sonosensitizer is used to form a vesicle containing a third colorant. As explained, a different sonosensitizer sensitive to a certain frequency range or other ultrasound parameter is used for each different colorant in an image. That way, any number of colors is used to recreate an image. In an embodiment, a composition includes one or more sonosensitive vesicles sensitive at different frequency ranges, wherein each sonosensitive vesicle that is sensitive to the same frequency range contains the same colorant. In an embodiment, vesicles with the same colorant are sensitive to the same ultrasound parameter. To recreate the image, the image is processed into a raster image, bitmap, or a dot matrix data structure, representing a rectangular grid of pixels or points of color. In an embodiment, each pixel has a different value of red, green and blue. Because the vesicles have been distributed over the area generally uniformly, the entire area is populated with actives of all different colors that represent each of the colors of the pixels. Then, in an embodiment, the 2D transducer array turns on those transducer elements in a manner to selectively release colorants that correspond to each pixel in the bitmap. For example, the 2D transducer array turns on those transducers to release the colorant red according to the bitmap. The 2D transducer array turns on those transducers to release the colorant green according to the bitmap. The 2D transducer array turns on those transducers to release the colorant blue according to the bitmap, thus recreating the image on living tissue. The method for releasing actives selectively via 2D ultrasound has many applications.

In an embodiment, vesicles are formed with more than one layer of amphipathic molecules. In an embodiment, a vesicle with more than one layer is formed so that each layer is formed with a different sonosensitizer, and each layer contains a different active or colorant. In an embodiment, a vesicle with more than one layer is formed so that each layer is sensitive to a different frequency of ultrasound. In an embodiment, therefore, a multi-layered vesicle is sensitive to different frequencies or any other ultrasound parameter. In an embodiment, an interior layer containing a first active is sensitive at a first frequency range, and the exterior layer containing a second active between the exterior and interior layers is sensitive at a second frequency range different than the first frequency range. Here, sensitivity to frequency can be replaced with any other ultrasound parameter. Frequency is being used to illustrate a representative embodiment. In an embodiment, a 2D ultrasound array applies the first frequency selectively to sensitize the interior layer to cause release of the first active to mix with the second active. In an embodiment, a 2D ultrasound array applies the first frequency selectively to cause the release of the first active to mix with the second active, wherein less than all of the transducer elements in the 2D ultrasound array apply the first frequency. In an embodiment, any number of transducer elements in the 2D ultrasound array apply the first frequency, and any number of transducer elements apply the second frequency, and the application of the first and second frequencies is carried simultaneously or in sequence in any order. In an embodiment, the number of different sonosensitive layers is not limited to two.

Accordingly, the embodiments describe recreating an image by applying ultrasound selectively to sonosensitive vesicles. In an embodiment, the composition includes sonosensitive vesicles that are sensitive at the same frequency, and the sonosensitive vesicles include the same colorant, such that by selectively turning on transducer elements in a pattern creates a bitone color image. In an embodiment, a composition includes sonosensitive vesicles that are sensitive to different frequencies, and the sonosensitive vesicles contain a plurality of different colorants, such that by selectively choosing frequencies or other ultrasound parameter for the individual transducer elements, in a pattern, an image having multiple colors is created. In an embodiment, a composition includes multilayered sonosensitive vesicles that contain two or more actives, such that by selectively choosing a frequency one or more of the layers is sensitized to cause release of the active to mix with other actives, before the frequency that sensitizes the exterior layer is applied to release the mixture of the actives.

In an embodiment, a liposome or other bilayer vesicle has two actives. In an embodiment, the first active in the exterior layer is a colorant that is released at a first frequency. In an embodiment, the second active of the interior layer is a pigment that when combined with the colorant in the first layer will produce a natural skin color of the living tissue. The second interior active is released at a second frequency. In this way, any unpleasant discoloration effects are minimized. In an embodiment, the second active generally hides the color of the first active by neutralizing, dissolving, or bleaching the first active.

In an embodiment, a first active and a second active are associated with a vesicle that has a relatively more stable interior layer and a less stable exterior layer. In an embodiment, the first active that produces the color is in the less stable exterior layer, and is therefore released first. The active being in the relatively more stable interior or central layer is therefore released at a later time. In an embodiment, the second active will neutralize the color caused by the first active. In an embodiment, the second active will boost, refresh or enhance the color caused by the first active. While color is used as to illustrate the embodiment, the provision for a vesicle with layers varying in stability is useful for other actives where a second active has a beneficial effect on the first active.

In an embodiment, a combination of the methods is applied. In an embodiment, the images that are created are used to create permanent or long-lasting cosmetics, such as eyeliner, blush, eyeshade, lip color, simulated tan, or cover irregularities in skin, and provide uniform skin color, and the like. In an embodiment, semi-permanent eyebrow or lip color is selectively removed with an ultrasonic transducer. In an embodiment, micelle inclusion of pigment or melanin is time selective. In an embodiment, the method is applied for the treatment of vitiligo. In an embodiment, the method is applied for artificial tanning. In an embodiment, the method is applied as cover-up for imperfections in the skin.

In an embodiment, the method illustrated in FIG. 6 is not used for creating images in living tissue. The method of delivering actives via the use of sonosensitive vesicles has many beneficial uses. In an embodiment, the method omits steps 402 and 408. In an embodiment, a method to deliver any active includes steps 404 and 406. In an embodiment, the active includes medicaments, therapeutic agents, lotions, balms, and the like. In an embodiment, the method is to be applied for pain management. In an embodiment, the method is applied for dermatological pharmaceuticals, such as acne vulgaris treatments. In an embodiment, the method is applied for hormone delivery. In an embodiment, the method is applied for stem cell delivery. In an embodiment, a microneedle array of various diameters and length is able to deposit the sonosensitive vesicles to a specific location and depth below the stratum corneum of a patient. The patient is then prescribed an ultrasound transducer, which the patient uses at a later time to according to a prescribed schedule or need. In this way, the patient is able to deliver a dose of medication according to a timed schedule.

In an embodiment, a peptide, protein, or ceramide is encapsulated in the interior aqueous environment (hydrophilic parts) of a reverse micelle, which will allow pH control of the environment during percutaneous delivery. The function and activity of a biologically active compound is often based on the pH or polarity of its local chemical environment, such as its solution. In an embodiment, this is true for proteins and peptides. There are a number of low residue number peptides (n=2 to 10) that show efficacy as cosmaceuticals and delivery into the epidermis or dermis in a controlled manner within a protective environment of the reverse micelle is highly desirable.

In an embodiment, a method of creating an image on living tissue include delivering a composition including a plurality of sonosensitive vesicles containing one or more image forming actives to living tissue. Non-limiting examples of image forming actives include ceramic oxides, chromophores, color additives, colorants, coloring agents, cosmetic color additives, dye precursors, dyes, inks, tattoo inks pigments, natural or artificial pigments, suspension of pigmented particles, and the like. Further non-limiting examples of image forming actives include temporary or permanents image forming actives, and the like. Further non-limiting examples of image forming actives include Food and Drug Administration (FDA)-approved color additives, dyes, inks pigments, and the like. Further non-limiting examples of image forming actives include dyes, pigments, inks, etc. complexed, carried, contained encapsulated, encased, entrapped, incorporated in microstructures, vesicles, and the like.

In an embodiment, a method of creating an image on living tissue include applying ultrasound selectively to the living tissue via a 2D ultrasound array to release the actives from the vesicles sensitive to the ultrasound energy and create an image on the living tissue.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method of creating an image on living tissue, comprising:
    with one or more processors, transforming a digital image into a set of commands to send control signals to individual transducer elements of a 2D ultrasound array;
    delivering a composition including a plurality of sonosensitive vesicles containing one or more image forming actives to living tissue; and
    applying ultrasound selectively to the living tissue via the 2D ultrasound array to release the actives from the vesicles sensitive to the ultrasound energy and create a reproduction of the image on the living tissue.

2. The method of claim 1, wherein delivering the composition including the plurality of sonosensitive vesicles containing one or more actives to living tissue includes delivering a composition including a plurality of sonosensitive vesicles containing one or more colorants.

3. The method of claim 1, wherein delivering the composition including the plurality of sonosensitive vesicles containing one or more actives to living tissue includes delivering a composition including a plurality of sonosensitive micelles, sonosensitive liposomes, sonosensitive hydrogels, sonosensitive niosomes, or sonosensitive hydrophobic polymers.

4. A method of creating an image on living tissue, comprising:
    delivering a composition including a plurality of sonosensitive vesicles containing one or more image forming actives to living tissue; and
    applying ultrasound selectively to the living tissue via a 2D ultrasound array to release the actives from the vesicles sensitive to the ultrasound energy and create an image on the living tissue, wherein delivering the composition including the plurality of sonosensitive vesicles containing one or more actives to living tissue includes delivering a composition including a first plurality of vesicles containing a first active and a second plurality of vesicles containing a second active.

5. The method of claim 4, wherein the first plurality of vesicles is sensitive to an ultrasound parameter of a first range, and the second plurality of vesicles is sensitive to an ultrasound parameter of a second range.

6. The method of claim 5, wherein the ultrasound parameter includes frequency, amplitude, power density, pulse period, or temperature.

7. A method of creating an image on living tissue, comprising:
    delivering a composition including a plurality of sonosensitive vesicles containing one or more image forming actives to living tissue; and
    applying ultrasound selectively to the living tissue via a 2D ultrasound array to release the actives from the vesicles sensitive to the ultrasound energy and create an image on the living tissue, wherein delivering the composition including the plurality of sonosensitive vesicles containing one or more actives to living tissue includes delivering a composition including a plurality of sonosensitive vesicles having an exterior layer and an interior layer, and a first active is contained on the inside of the interior layer, and a second active is contained between the exterior and interior layer, and the method further comprises applying ultrasound at a frequency range to release the first active from the interior layer to mix with the second active within the exterior layer.

8. The method of claim 7, wherein the first active is a first color and the second active is a second color, wherein mixing of the first and second actives produces a third color.

9. A method of creating an image on living tissue, comprising:
delivering a composition including a plurality of sonosensitive vesicles containing one or more image forming actives to living tissue; and
applying ultrasound selectively to the living tissue via a 2D ultrasound array to release the actives from the vesicles sensitive to the ultrasound energy and create an image on the living tissue, wherein delivering the composition including the plurality of sonosensitive vesicles containing one or more actives to living tissue includes delivering a composition including a plurality of sonosensitive vesicles having an exterior layer and an interior layer, and a first active is contained on the inside of the interior layer, and a second active is contained between the exterior and interior layers, and the method further comprises applying ultrasound at a first frequency range to release the second active from between the interior and exterior layers to form the image in the living tissue.

10. The method of claim 9, further comprising:
applying ultrasound at a second frequency range to release the first active, which neutralizes the second active in the living tissue.

11. The method of claim 1, wherein applying ultrasound selectively to the living tissue via the 2D ultrasound array to release the actives from the vesicles sensitive to the ultrasound energy and create an image on the living tissue includes applying an ultrasound stimulus having a frequency greater than 20 kilohertz.

12. A method of dispensing an active to living tissue, comprising:
dispensing into living tissue a plurality of sonosensitive vesicles containing an active, wherein the vesicles are dispensed into the living tissue via a plurality of microneedles varying in diameter or length or both diameter and length; and
applying ultrasound selectively to the living tissue via a 2D ultrasound transducer array.

13. The method of claim 12, further comprising depositing vesicles at more than one depth in the living tissue.

14. The method of claim 13, further comprising adjusting a focal length of the 2D ultrasound transducer array to target vesicles at a first depth.

15. The method of claim 12, further comprising depositing vesicles over an area at the same depth, wherein higher concentrations of vesicles are created in the area.

16. The method of claim 15, further comprising selectively turning on 2D transducer array elements to target the areas having a greater concentration of vesicles.

17. The method of claim 12, further comprising adjusting a frequency of the 2D transducer array to sensitize less than all the vesicles to cause a release of actives.

18. The method of claim 12, wherein the vesicles include micelles, reverse micelles, liposomes, niosomes, hydrogels, hydrophobic polymers, or any combination thereof.

* * * * *